(12) United States Patent
Fisker

(10) Patent No.: US 10,311,162 B2
(45) Date of Patent: Jun. 4, 2019

(54) CUSTOMIZED DENTAL IMPRESSION TRAY

(75) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 1320 days.

(21) Appl. No.: 14/235,197

(22) PCT Filed: Jun. 29, 2012

(86) PCT No.: PCT/EP2012/062684
§ 371 (c)(1),
(2), (4) Date: May 13, 2014

(87) PCT Pub. No.: WO2013/026600
PCT Pub. Date: Feb. 28, 2013

(65) Prior Publication Data
US 2014/0277665 A1    Sep. 18, 2014

Related U.S. Application Data

(60) Provisional application No. 61/513,194, filed on Jul. 29, 2011.

(30) Foreign Application Priority Data

Sep. 21, 2011    (DK) ................. 2011 00721

(51) Int. Cl.
*A61C 7/02*    (2006.01)
*G06F 17/50*    (2006.01)
*A61C 9/00*    (2006.01)
*A61C 13/00*    (2006.01)

(52) U.S. Cl.
CPC ............ *G06F 17/50* (2013.01); *A61C 9/0006* (2013.01); *A61C 9/004* (2013.01); *A61C 13/0004* (2013.01)

(58) Field of Classification Search
CPC ...................................................... G06F 17/50
See application file for complete search history.

(56) References Cited

U.S. PATENT DOCUMENTS

| 4,401,616 A * | 8/1983 | Wagner ............... A61C 9/0006 |
| | | 264/138 |
| 5,112,225 A | 5/1992 | Diesso |
| 7,802,987 B1 | 9/2010 | Phan |
| 2004/0038183 A1 | 2/2004 | Jacobs et al. |

(Continued)

FOREIGN PATENT DOCUMENTS

| GB | 2329341 A | 3/1999 |
| WO | WO 2008/051129 A1 | 5/2008 |

OTHER PUBLICATIONS

International Search Report (PCT/ISA/210) dated Nov. 19, 2012, by the European Patent Office as the International Searching Authority for International Application No. PCT/EP2012/062684.

*Primary Examiner* — Brian W Wathen
*Assistant Examiner* — Abdou K Seye
(74) *Attorney, Agent, or Firm* — Buchanan Ingersoll & Rooney P.C.

(57) ABSTRACT

Disclosed are methods and systems for generating a virtual model of a customized impression tray and for manufacturing such a customized impression tray. A 3D digital representation of a patient's set of teeth is obtained and a virtual model of the customized impression tray is generated, where the generating comprises shaping the virtual model of the customized impression tray according to the 3D digital representation.

21 Claims, 8 Drawing Sheets

(56) References Cited

U.S. PATENT DOCUMENTS

| | | |
|---|---|---|
| 2005/0181334 A1 | 8/2005 | Jacobs |
| 2005/0239013 A1* | 10/2005 | Sachdeva ............... A61C 7/146 433/24 |
| 2005/0271996 A1* | 12/2005 | Sporbert ................. A61C 7/00 433/24 |
| 2008/0026338 A1* | 1/2008 | Cinader ................. A61C 1/084 433/29 |
| 2008/0233528 A1 | 9/2008 | Kim et al. |
| 2009/0017410 A1* | 1/2009 | Raby ...................... A61C 7/002 433/2 |
| 2009/0291416 A1* | 11/2009 | Brunson .............. A61C 9/0006 433/215 |
| 2010/0183998 A1* | 7/2010 | Poirier ................... A61C 1/084 433/72 |
| 2010/0223034 A1* | 9/2010 | Imgrund ................. A61C 7/00 703/1 |
| 2010/0297572 A1 | 11/2010 | Kim |
| 2011/0091832 A1* | 4/2011 | Kim ...................... A61C 7/002 433/3 |
| 2011/0171593 A1 | 7/2011 | Ross |
| 2012/0179281 A1* | 7/2012 | Steingart ............ A61C 13/0004 700/97 |

* cited by examiner

CUSTOMIZED DENTAL IMPRESSION TRAY

This invention generally relates to a customized impression tray for obtaining dental impressions of teeth in a patient's mouth. More particularly, the invention relates to a method for generating a virtual model of or manufacturing such a customized impression tray, and a system for implementing the method.

Manufacturing the customized impression tray from a virtual model which is generated from a 3D digital representation of the patient's teeth potentially provides that the manufactured customized impression tray fits more precisely to the teeth than a standard one-size-fits-all impression tray. The impression tray can hence be customized to fit the set of teeth of the individual patient, such that discomfort for the patient while obtaining an impression of the teeth and/or the use of impression material may be reduced.

The placement of an impression tray in the patient's mouth is rarely a comfortable experience and the discomfort is increased when the tray does not fit the patient's teeth. Consequently, it is an advantage that the impression tray is customized to fit the set of teeth of individual patients One advantage of the method according to the present invention is that the customized impression tray can be designed faster and with a higher precision compared to prior art methods, such as fully manual methods. The manufacturing step may be more time consuming, but this task can be handled automatically by e.g. rapid prototyping equipment, such that the total operator time for each impression tray is reduced significantly.

Disclosed is a method of manufacturing a customized impression tray adapted for being used in relation to obtaining an impression of a set of teeth where the customized impression tray comprises a lingual side-wall and a labial side-wall, said method comprising:
a): obtaining a 3D digital representation of the set of teeth, where said 3D digital representation comprises a labial surface and a lingual surface of the set of teeth;
b): generating a virtual model of the customized impression tray, where the virtual model comprises portions corresponding to tooth-facing surfaces of the labial and lingual side-walls, and where said generating comprises shaping the virtual model of the customized impression tray according to the 3D digital representation; and
c): manufacturing the customized impression tray from said virtual model.

In the context of the present invention, the phrase "labial surface" is used to describe all tooth surfaces facing away from the patient's tongue, such that this phrase also covers the buccal surfaces of the teeth.

In the context of the present invention, the phrase "labial side-wall" is used to describe the entire side-wall of the customized impression tray which is configured to be arranged opposite to the patient's tongue relative to the teeth, such that this phrase also covers a side-wall at the patient's buccal tissue when the customized impression tray comprises a part at the patient's buccal tissue.

When a customized impression tray is manufactured from the generated virtual model, the virtual model and the manufactured customized impression tray has at least some corresponding features, such as e.g. corresponding surfaces and side-walls.

For a given surface of the manufactured customized impression tray the virtual model may have a corresponding portion, such that when this portion is shaped according to a preferred shape, the corresponding surface of the manufactured tray can take substantially the same shape depending on choice and precision of manufacturing technique.

The generated virtual model preferably comprises portions that form virtual side-walls which define the shape of the side-walls of the manufactured customized impression tray. For example, the virtual model may comprise portions forming a virtual labial side-walls and portions forming a virtual lingual side-wall The portions of the generated virtual model may be considered to be virtual surfaces corresponding to physical surfaces of a manufactured customized impression tray, such as e.g. the tooth-facing surfaces of the side-walls of the customized impression tray. The phrase "virtual tooth facing surface" can be used instead of "the portion of the virtual model corresponding to the tooth-facing surface".

In the context of the present invention, the phrase "shaping the virtual model of the customized impression tray according to the 3D digital representation" specifies that the virtual model is generated such that is takes into account the surfaces of the set of teeth. The surfaces may e.g. be tooth surfaces or gingiva surfaces that are included in the 3D digital representation of the set of teeth. This provides that the customized impression tray manufactured from the generated virtual model has a shape that takes into account the patient's set of teeth such that the use of the customized impression potentially involves significantly less discomfort for the patient compared to the case where a standard tray is used.

The virtual model is configured to provide that the manufactured customized impression tray at least partly encloses a space in which a volume of an impression material may be placed such that an impression of a set of teeth can be obtained in the impression material when placing the manufactured customized impression tray in relation to the patient's set of teeth. The lingual and labial side-walls of the customized impression tray may be arranged to define a groove in the customized impression tray, where said grove corresponds at to the least partly enclosed space.

In some embodiments, the customized impression tray at least partly has the shape of an arch, such that it can be arranged in relation to a patient's set of teeth with the arch of the tray being substantially aligned with the arch of the set of teeth. In the context of the present invention, the phrase "an arch" may be used in relation to both a full arch and a partial arch.

The set of teeth may comprise all the mandibular or the maxillar teeth such that the set of teeth provides the full arch, or the set of teeth may comprise part of all the mandibular or the maxillar teeth such that the set of teeth provides a partial arch.

The customized impression tray may be configured for obtaining an impression of all the mandibular or of all the maxillar teeth such that the arch of the customized impression tray describes a full arch, or the customized impression tray may be configured for obtaining an impression of a part of the mandibular or a part of the maxillar teeth such that the arch of the customized impression tray describes a partial arch.

Disclosed is a method for generating a virtual model of a customized impression tray comprising labial and lingual side-walls, where said customized impression tray is for obtaining an impression of a set of teeth, said method comprising:
a): obtaining a 3D digital representation of the set of teeth, where said 3D digital representation comprises a labial surface and a lingual surface of the set of teeth; and b): generating the virtual model of the customized impression tray, where the virtual model comprises portions corresponding to tooth-facing surfaces of the labial and lingual side-walls, and where said generating comprises shaping the virtual model of the customized impression tray according to the 3D digital representation A customized impression tray may be manufactured from the virtual model such that the impression tray is customized to fit the set of teeth of individual patient's.

According to an object of the invention is disclosed a method of manufacturing a customized impression tray adapted for being used in relation to obtaining an impression of a set of teeth where the customized impression tray comprises a lingual side-wall and a labial side-wall, said method comprising:

a): obtaining a 3D digital representation of the set of teeth, where said 3D digital representation comprises a labial surface and a lingual surface of the set of teeth;

b): generating a virtual model of the customized impression tray, where the virtual model comprises portions corresponding to tooth-facing surfaces of the labial and lingual side-walls, and where said generating comprises shaping the virtual model of the customized impression tray according to the 3D digital representation; and c): manufacturing the customized impression tray from said virtual model.

Disclosed is a system for manufacturing a customized impression tray adapted for being used in relation to obtaining an impression of a set of teeth, where the customized impression tray comprises a lingual side-wall and a labial side-wall, said system comprising a): a non-transitory computer readable medium having one or more computer instructions stored thereon, where said computer instructions comprises instructions for generating a virtual model of the customized impression tray, where the virtual model comprises portions corresponding to tooth-facing surfaces of the labial and lingual side-walls, where said generating comprises shaping the virtual model of the customized impression tray according to a 3D digital representation of the set of teeth, and where said 3D digital representation comprises a labial surface and a lingual surface of the set of teeth; and b): a manufacturing device configured for manufacturing the customized impression tray from said virtual model.

Disclosed is a system for generating a virtual model of a customized impression tray for obtaining an impression of a set of teeth, where the customized impression tray comprises labial and lingual side-walls, where the system comprises:

a non-transitory computer readable medium having one or more computer instructions stored thereon, where said computer instructions comprises instructions for generating a virtual model of the customized impression tray, where the virtual model comprises portions corresponding to tooth-facing surfaces of the labial and lingual side-walls, where said generating comprises shaping the virtual model of the customized impression tray according to a 3D digital representation of the set of teeth, and where said 3D digital representation comprises a labial surface and a lingual surface of the set of teeth.

In some embodiments, the shaping comprises shaping the portion of the virtual model corresponding to the tooth-facing surface of the labial side-wall.

In some embodiments, the shaping comprises shaping the portion of the virtual model corresponding to the tooth-facing surface of the lingual side-wall.

In some embodiments, shaping the portions of the virtual model corresponding to the tooth-facing surfaces of the labial and lingual side-walls comprises defining the form of each tooth-facing surface and/or the position of the tooth-facing surfaces relative to each other and/or relative to a centerline of the customized impression tray. The form and/or relative position of the surfaces in the manufactured customized impression tray are defined at least in part by the virtual model of the customized impression tray. The shaping preferably comprises adapting the virtual model of the customized impression tray such that the customized impression tray manufactured from the virtual model has a desired shape.

In the context of the present invention, the phrase "the centerline" may refer to a line at the center of the space enclosed by the lingual and labial side-walls of the customized impression tray. The centerline may extend along the arch of the tray. The centerline may substantially follow the arch of the set of teeth when the manufactured customized impression tray is arranged relative to the patient's set of teeth.

In some embodiments, the method comprises defining one or more virtual planes in relation to the digital 3D representation, where the virtual model is shaped based on the one or more virtual planes.

In some embodiments, the virtual planes are shaped according to the lingual or labial surfaces of the teeth such that undulations along the arch according to the teeth are present in the virtual planes. The one or more virtual planes may also be smooth along the arch. This can e.g. be obtained by providing a smoothed teeth surface as the initial version of the virtual plane.

In some embodiments, an offset away from the corresponding teeth in the digital 3D representation is provided to the one or more virtual planes, such that the virtual model is shaped based on the one or more offset virtual planes. The offset away from the teeth in the digital 3D representation corresponds to an offset away from a centerline of the virtual model of the customized impression tray, such that the wall-to-wall distance may increase with such an offset. For a labial and/or lingual offset the wall-to-wall distance can increase with the offset In some embodiments, the virtual plane is at least in part defined by virtually blocking out undercut regions at the 3D digital representation of the set of teeth. At the blocked-out surface the virtual plane may coincide with the surface generated by the virtual blocking out. At the occlusal/incisal edges of the teeth, the virtual plane may be formed by extending the blocked-out surface along the longitudinal axis of the corresponding teeth.

In some embodiments, the shape and the relative position of the portions of the virtual model relating to the tooth-facing surfaces of the side-walls is determined from such virtual planes, where the virtual planes may be determined in one or more steps from the 3D digital representation of the set of teeth. These steps may include a step of virtually blocking out undercut regions of the digital 3D representation and a step of offsetting the virtual plane created at least in part from the blocking out of the undercut regions.

The offset of the virtual planes may provide that the tooth-facing surfaces of the side-walls are offset away from the set of teeth such that the wall-to-wall distance is increased.

In some embodiments, the shaping is configured for providing that a wall-to-wall distance between portions of the virtual model relating to opposing tooth-facing surfaces of the labial side-wall and lingual side-wall is based on the digital 3D representation.

In some embodiments, this is provided by determining a virtual plane based on the digital 3D representation of the set of teeth. The virtual plane may be defined from a virtual block out of undercut regions in the digital 3D representation and an offset of the surface formed by the block out.

In the context of the present invention, the phrase "opposing tooth-facing surfaces" may refer to surfaces that are located at the same position along the arch of the set of teeth with surfaces facing each other.

In the context of the present invention, the phrase "along the set of teeth" may be used in relation to different positions along the arch of the set of teeth. The phrase may e.g. be used in relation to describing variations in the width of the set of teeth when following the arch from one tooth to another. The width of an element may be measured along an axis which is perpendicular to a section of the arch of the set of teeth, where the axis is in a plane that is substantially parallel to the occlusal plane of the set of teeth.

The width of a section of the set of teeth may hence be measured along an axis which is perpendicular to the arch at said section of the set of teeth, where the axis is substantially parallel to the occlusal plane of the set of teeth.

The width of a section of the set of teeth may change along the longitudinal axis of the set of teeth due to the natural concave shape of teeth.

In some embodiments, the virtual model of the customized impression tray is generated directly from the 3D digital representation of the set of teeth or by deriving parameters from the 3D digital representation.

In some sections of the text, the customized impression tray is described with reference to the set of teeth or to the 3D digital representation of the set of teeth. When such references are made, it may be contemplated that the virtual model of the customized impression tray is arranged in relation to the 3D digital representation of the set of teeth or that the manufactured customized impression tray is arranged in relation to the set of teeth, such as when the manufactured customized impression tray is arranged in relation to the set of teeth in order to obtain an impression of the set of teeth.

When the phrase "the width" is used in relation to an element of the customized impression tray, it may refer to the dimension of that element along an axis that is substantially parallel to the axis that the width of the set of teeth is measured along. In the measurement, it is contemplated that the customized impression tray is arranged in relation to the set of teeth.

In the context of the present invention, the phrase "the height" of an element may be measured along an axis that corresponds to the longitudinal axis of the set of teeth. That is, the height of a tooth may be measured along the longitudinal axis of the tooth, or the height of an element of the customized impression tray may be measured along the longitudinal axis of a tooth in the set of teeth. In the measurement of the height of an element of the customized impression tray, it is contemplated that the customized impression tray is arranged in relation to the set of teeth. The height of a side-wall of the customized impression tray may be measured along a axis extending from the gingiva facing part of the side-wall to a base-wall at the opposite end of the side-wall.

The base-wall of the customized impression tray may also be referred to as an occlusal side-wall, and the phrases "base-wall" and "occlusal side-wall" may be used interchangeably.

In some embodiments, the wall-to-wall distance changes along the height of the customized impression tray. The change in the wall-to-wall distance along the height of the customized impression tray may be such that the wall-to-wall distance is larger at the gingiva facing edge of the side walls than at the region facing the cusp or incisal edge of the teeth when the customized impression tray is arranged in relation to the set of teeth. That is, there may be an increase in the wall-to-wall distance towards the root end of the tooth compared to the distance at the cusp of the tooth when the customized impression tray is arranged in relation to the set of teeth.

In the context of the present invention, the phrase "the longitudinal axis of the teeth" may refer to an axis extending from the root end of the tooth end to the cusp or incisal edge of the tooth.

The rounded form of the teeth may cause variations in the width of the 3D digital representation along the set of teeth. In order to accommodate for such variations, the wall-to-wall distance may be determined from an average distance for each section of the set of teeth, such as for each tooth. The wall-to-wall distance may change smoothly along the set of teeth where the wall-to-wall distance is correlated with the average distance.

The cross sectional dimension of a molar tooth perpendicular to the centerline is larger than that of an anterior tooth, and the wall-to-wall distance may hence be smaller at the anterior teeth than at the molar teeth if a substantially constant gap between the teeth and the teeth-facing surfaces of the customized impression tray is desired.

In some embodiments, the wall-to-wall distance is based on the 3D digital representation over sections of the set of teeth or along the entire set of teeth.

In some embodiments, shaping the portions of the virtual model relating to the tooth-facing surfaces provides that the tooth-facing surfaces in a customized impression tray manufactured from the virtual model are shaped to allow for a controlled distance from the labial and lingual surfaces of the set of teeth when the manufactured customized impression tray is arranged in the mouth of the patient.

The controlled distances may be uniform along the arch of the set of teeth such that the portions of the virtual model relating to the tooth-facing surfaces duplicates the geometry of the corresponding portions of the digital 3D representation.

The portions of the virtual model relating to the tooth-facing surfaces may be smooth such that the controlled distance has local maxima at indentations in the digital 3D representation of the set of teeth occurring at interproximal regions, e.g. between two neighboring molar teeth.

In some embodiments, the shaping comprises controlling said wall-to-wall distance, where the wall-to-wall distance can be controlled through the relative positions of the portions of the virtual model relating to the tooth-facing surfaces.

In some embodiments, said wall-to-wall distance is at least in part defined by an offset of the one or more virtual planes away from a centerline of the customized impression tray, i.e. from a centerline of the virtual model.

In some embodiments, the offset of the virtual plane provides a shift in the virtual position of the tooth-facing surfaces of the virtual model corresponding to an increase in the wall-to-wall distance. This may correspond to a movement of the virtual tooth-facing surfaces of the virtual model away from the surfaces of the teeth described by the 3D digital representation of the set of teeth.

For the manufactured customized impression tray arranged in relation to the set of teeth, such an offset may correspond to a displacement of the tooth-facing surfaces such that space is provided for the impression material between the set of teeth and the manufactured customized impression tray.

For the manufactured customized impression tray arranged in relation to the set of teeth such an offset may correspond to a displacement of the tooth-facing surfaces providing a gap between the set of teeth and the customized impression tray.

In some embodiments, the offset corresponds to a shelling of a region of the digital 3D representation of the set of teeth. The shelling may be configured to provide a uniform distance between surface of teeth, such as occlusal, lingual or labial surfaces, and the opposing surface of the side-walls of the manufactured customized dental impression tray. The shelled region may comprise a least part of the teeth of the patient's mandibular or maxillary arch.

In some embodiments, generating the virtual model comprises defining initial positions and shapes of the virtual tooth-facing surfaces and subsequently modifying these initial positions and shapes to provide final positions and shapes.

In some embodiments, generating the virtual model comprises defining initial positions and shapes of the virtual planes and subsequently modifying these initial positions and shapes to provide final positions and shapes.

The initial positions of the virtual tooth-facing surfaces and/or of the virtual planes may be defined based on the minimum wall-to-wall distance as determined from the local cross-sectional width of the set of teeth. The local cross-sectional width at one tooth may be defined at the widest portion of this tooth. The minimum wall-to-wall distance may change along the arch due to the change in size and shape of the teeth along the arch.

The initial positions and shapes of the virtual tooth-facing surfaces may be defined from virtual planes that just contact the set of teeth and generating the virtual model may comprise offsetting these virtual planes away from the 3D digital representation of the set of teeth. These virtual planes may be flat or curved e.g. to accommodate for the shape of individual teeth.

The virtual tooth-facing surfaces of the side-walls may be determined from said virtual planes, such that an offset of the virtual plane provides an offset of the virtual tooth-facing surfaces. The offset may be such that it corresponds to an offset of the tooth-facing surfaces of the manufactured customized impression tray away from a centerline of the customized impression tray.

The offset may provide that a gap is established between the 3D digital representation of the set of teeth and the virtual model of the customized impression tray when the two are arranged in relation to each other, such as in a combined virtual model or in a visual representation of the two arranged such as when an impression is taken. This gap may provide space for impression material between the tooth-facing surfaces of the manufactured customized impression tray and the set of teeth when the customized impression tray is used for obtaining an impression of the set of teeth.

One advantage of the present invention over the prior art is that the gap or the distance between the set of teeth and the manufactured customized impression tray can be controlled quite accurately by an operator such that high-quality impressions can be obtained and so that the discomfort of the patient is reduced compared to when using standard sized impression trays.

In some embodiments, the offset comprises a lingual offset. The lingual offset may correspond to an offset of the tooth-facing surface of the lingual side-wall away from the lingual surface of the set of teeth if the remaining parts of the customized impression tray are kept at a fixed arrangement relative to the set of teeth.

In some embodiments, the offset comprises a labial offset. The labial offset may correspond to an offset of the tooth-facing surface of the labial side-wall away from the labial surface of the set of teeth if the remaining parts of the customized impression tray are kept at a fixed arrangement relative to the set of teeth.

In some embodiments, the offset comprises an occlusal offset. The occlusal offset may correspond to displacing a tooth-facing surface facing the cusp or the incisal edge of the teeth, such as a base-wall, away from the location in which the teeth are positioned when the customized impression tray is arranged in relation to the patient's set of teeth, while maintaining other parts of the virtual model fixed relative to the location.

The lingual offset and/or the labial offset may be measured relative to the centerline of the customized impression tray, such as measured along an axis which is parallel to the occlusal plane and perpendicular to the centerline In some embodiments, the lingual offset and/or the labial offset and/or the occlusal offset is in the range of about 0.5 mm to about 5 mm, such as in the range of about 1 mm to about 4 mm, such as in the range of about 2 mm to about 3 mm.

For a virtual model where the portions relating to the tooth facing surfaces of the customized impression tray are smooth compared to the digital 3D representation of the set of teeth, such that the tooth facing surface does not duplicate the corresponding surface of the digital 3D representation, the maximum size of the lingual offset and/or the labial offset in the range of about 0.5 mm to about 5 mm, such as in the range of about 1 mm to about 4 mm, such as in the range of about 2 mm to about 3 mm.

Some teeth have a smaller cross section at some positions along the height of the tooth than at e.g. the cusp of the tooth. This may introduce undercuts regions, i.e. regions which cannot be seen when the tooth is viewed from the occlusal plane of the patient.

In some embodiments, the wall-to-wall distance is at least in part defined by virtually blocking out undercut regions at the 3D digital representation of the set of teeth. The virtually blocking out the undercut regions may define the initial position and shape of the virtual planes such that the virtual planes coincide with the 3D digital representation of set of teeth at the apex of curved surfaces of the labial and/or lingual surfaces of the teeth.

The virtual plane may be offset from an initial position defined by the virtually blocked-out surface of the 3D digital representation to provide the offset virtual plane from which the tooth-facing surfaces of the customized impression tray are defined.

The virtual plane may be determined from an offset of the virtually blocked out surface of the 3D digital representation.

The blocking-out may be configured to provide that undercuts regions are avoided e.g. near the gingiva for concave teeth surfaces. The blocking out may define a virtually blocked out surface, and this surface may be offset to provide the offset virtual plane from which the tooth-facing surfaces of said side-walls are defined. This may be equivalent to forming the virtual plane from the blocked-out surface and offsetting the formed virtual plane to provide the offset virtual plane.

In some embodiments, the method comprises determining the undercut regions based on a selected insertion direction of the customized impression tray. One insertion direction may be defined for both the mandibular teeth and one for the maxillary teeth. The virtually blocking out undercut regions may be provided by virtually filling regions to which there is no line of sight along the insertion direction.

Blocking out undercuts in said set of teeth may be realized by adding a virtually layer to the 3D digital representation. The layer may be thicker at the closer to the gingival than at the occlusal plane of the set of teeth or it may have a substantially uniform thickness over the surface of the tooth.

If the virtual model of the customized impression tray is generated without providing that undercut regions are avoided, the manufactured customized impression tray may be such that it will extend into the undercut regions. This may make it difficult to remove the customized impression tray from the set of teeth when the impression is obtained.

When generating the virtual model of the customized impression tray, the virtual model may be visualised as part of combined virtual model comprising the virtual model of the customized impression tray and the 3D digital representation of the set of teeth. In such a combined model, the wall-to-wall distance between the labial and lingual surface of the teeth and the tooth-facing surfaces of the side-walls of the customized impression tray is visualized and in some embodiments, the operator is allowed to control the distance.

In some embodiments, the shaping of the virtual model comprises adjusting a template virtual model of an impression tray such that the arch or centerline of the virtual model follows the corresponding arch of the digital 3D representation of the set of teeth. The virtual side-wall of the template virtual model are then adjusted according to the adjustment of the arch.

In some embodiments, the virtual tooth-facing surfaces of the side-walls are formed by modifying the virtual side-walls in a tray template selected e.g. from a tray library. The modifying of the virtual side-walls may comprise providing an offset to the virtual side-walls relative to the position where teeth will be present when the customized impression tray is in use.

In some embodiments, the virtual tooth-facing surfaces of the side-walls is generated based on the 3D digital representation of the set of teeth. This may be realized by selecting parts of the 3D digital representation corresponding to one or more specific sections of the surface of the teeth, where these parts or sections may be identified by an operator or automatically using algorithms known by the skilled person. Such a part or a section may be defined by the cross-section of the teeth measured where the teeth have the largest cross sectional area. The cross section may be substantially perpendicular to the longitudinal axis of the tooth.

In some embodiments, the heights of the tooth-facing surfaces of the labial and/or the lingual side walls are determined from the 3D digital representation of the set of teeth. The height of the tooth-facing surfaces may vary along the arch of the customized impression tray. This variation in the height may be arranged to accommodate for variations in the height of the teeth.

The side-walls of the customized impression tray may each comprise a gingiva-facing part which is facing the patient's gingiva when the customized impression tray is arranged in relation to the patient's set of teeth. The gingiva-facing part may be the part or edge which is closest to the gingiva.

The height of the tooth-facing surface of the labial side-wall of the customized impression tray may be defined as the distance from the tooth-facing surface of an occlusal side-wall to the gingiva-facing part of the labial side-wall.

The height of the tooth-facing surface of the lingual side-wall of the customized impression tray may be defined as the distance from the tooth-facing surface of an occlusal side-wall to the gingiva-facing part of the lingual side-wall.

The method may comprise manually determining the shape of the portion of the virtual model relating to a gingiva-facing part of the labial side wall and/or of the lingual side wall. The shape may be determined manually by marking relevant positions on a visualization of the digital 3D representation of the set of teeth. The shape may be determined automatically using software implemented algorithms configured for identifying a relevant shape of the portion of the virtual model relating to a gingiva-facing of the labial side-wall and/or of the lingual side-wall.

The method may comprise automatically determining the shape of portion relating to the gingiva-facing part of the labial side wall and/or of the lingual side wall. This may be realized using e.g. computer implemented algorithms known to the skilled person.

In some embodiments, the shape of a portion of the virtual model relating to the gingiva-facing part of the labial side wall and/or of the lingual side wall is described by a 3D spline. The 3D spline may be visualized together with a visual presentation of the 3D digital representation of the set of teeth, such as visualized on a graphical display unit, such as a computer screen.

The 3D spline may be derived from the 3D digital representation of the set of teeth, such as derived automatically from the 3D digital representation.

The 3D spline may be formed from one or more sections of the margin line of the set of teeth, where the margin line may be extracted from the 3D digital representation of the set of teeth. The 3D spline may be formed from sections of the margin line located e.g. at the center of the individual teeth with one section for each tooth in the set of teeth. The 3D spline may be offset from the occlusal plane towards or away from the base wall.

The 3D digital representation may be obtained by scanning a physical model or an impression of the set of teeth where the shape of the gingiva-facing part of the customized impression tray is indicated by one or more lines drawn on the physical model or impression. The shape of the drawn lines may be translated into a 3D spline.

The 3D spline may be projected onto the 3D digital representation and the result may be visualized.

The 3D spline may be derived manually from the 3D digital representation. The 3D digital representation of the set of teeth may be visualized using a graphical display unit such that an operator manually can mark the 3D spline, segments of the 3D spline and/or points between which the 3D spline extends using e.g. a pointing tool. The 3D spline may be formed based on the position of these points or segment relative to the 3D digital representation.

The 3D spline may be visualized together with a visual presentation of the 3D digital representation of the set of teeth.

The 3D spline may be adjusted manually by an operator using a pointing tool and a graphical display unit. This may for instance be realized using a graphical display unit and a pointer tool, such as a mouse, where points on or segments of the 3D spline are defined and/or moved relative to the 3D digital representation.

The graphical display unit may be a computer screen and the pointing tool may be a mouse.

In some embodiments, the customized impression tray is adapted for use in relation to a dental implant procedure. The design of the virtual model of the customized impression tray may then take into account the implant location and implant orientation. The implant location and implant orientation may be determined from the digital 3D representation of the patient's set of teeth.

In some embodiments, the method comprises defining an opening in the virtual model of the customized impression tray at the part corresponding to the implant position, i.e. the part of virtual model which in the manufactured customized impression tray is configured to be located at the implant position when the tray is arranged in relation to the patient's set of teeth. The opening in the virtual model is configured to provide that the corresponding opening in the manufactured customized impression tray allows access to e.g. an impression abutment or impression coping mounted in the implant for transferring the position of the implant from the patient's mouth to the impression.

In some embodiments, the size and location of the opening is determined from an implant treatment plan.

In some embodiments, the implant treatment plan comprises planning the position and orientation of the implant in the patient's mouth. In such cases, the customized impression tray can be designed and manufactured at the onset of the implant treatment, i.e. before the implant is arranged in the patient's mouth.

In some embodiments, the implant treatment plan comprises designing a drill guide configured for guiding the drilling of the implant hole.

In some embodiments, the implant treatment plan comprises determining the actual implant position and the implant orientation in the patient's mouth, i.e. the position and orientation of the implant that physically is placed in the patient's mouth.

In some embodiments, the opening is defined by subtracting a cylinder from the virtual model of the customized impression tray, where said cylinder is aligned with the implant. The cylinder may be arranged according to the orientation and/or position of the implant. The subtraction of the cylinder may comprise identifying regions of the virtual model of the customized impression tray which overlaps with the cylinder and deleting these regions in the virtual model.

In some embodiments, the opening is designed to be larger than its ideal size to account for inaccuracies in the implant orientation and/or position. Such inaccuracies may be relative to the planned implant orientation and/or position and may occur during the drilling of the hole into which the implant is to be placed.

The cross section of the cylinder may be selected from the group comprises a circle, an ellipse, a parabola, a hyperbola, a rectangle, a square, or a triangle.

In some embodiments, the long axis of the cylinder cross section is aligned with the direction along which the largest inaccuracy in the implant position and orientation is expected. This may be along a direction which is substantially parallel with the arch at the implant position.

The opening may be defined automatically based on the implant position and/or orientation.

An implant treatment plan may comprise selecting the position and orientation of the implant in the set of teeth. The size and/or position of the opening may then be determined automatically based the planned position and orientation of the implant and how the customized impression tray is to be arranged in relation to the set of teeth.

The opening may be described by an opening 3D spline. This opening 3D spline may be manipulated in the same manner as the 3D spline describing the gingiva-facing part of the side-walls.

The dental implant may be for supporting a replacement tooth or an implant-supported bridge. An implant-supported bridge may be supported by two or more implants. An opening may then be defined in the customized impression tray for each dental-implant.

In some embodiments, the method comprises determining the arch of the set of teeth from said 3D digital representation and based on that arch define the centerline or the arch of the virtual model of the customized impression tray.

The arch of the customized impression tray may be shaped to be substantially identical to the arch of the set of teeth, such that the arch of the set of teeth may follow the arch of the customized impression tray when the two are arranged relative to each other.

In some embodiments, the 3D digital representation of the set of teeth is obtained by scanning a physical model or an impression of the set of teeth or by direct internal scanning.

The 3D digital representation of the set of teeth may e.g. be obtained as part of a pre-treatment procedure, such as during the initial preparation of a dental implant procedure.

The scanning may be performed by means of laser light scanning, white light scanning, probe-scanning, X-ray scanning, and/or CT scanning.

The labial and/or lingual surfaces of the digital 3D representation of the set of teeth preferably relates to tooth surfaces of the patient's set of teeth and/or gingival surfaces, such that the 3D digital representation of the set of teeth comprises data relating to the patient's teeth and/or gingiva.

In some embodiments, an expected position and/or orientation of the implant is estimated from the obtained 3D digital representation of the set of teeth.

The 3D digital representation of the set of teeth may be obtained using a pressure sensitive device configured to detect the distribution of the pressure provided by the set of teeth during a bite. The pressure sensitive device may comprise a sheet of pressure deformable material with a thickness of a few millimeters. This sheet may then be scanned to provide the 3D digital representation of the set of teeth. The resulting 3D digital representation may only provide data relating to the very first millimeters of the teeth as measured from their cusp, but this may be sufficient to determine the arch of the set of teeth. The pressure sensitive device may be configured for obtaining their 3D digital representation directly based on an electronic registration of the pressure applied to the set of teeth.

In some embodiments, the customized impression tray is manufactured from said virtual model using a rapid prototyping system, such as a direct printing system or a milling system.

In some embodiments, the method comprises combining the 3D digital representation and the virtual model of the customized impression tray to obtain a combined virtual model.

In the combined virtual model, the relative arrangement of the virtual model of the customized impression tray and the 3D digital representation of the set of teeth may correspond to a preferred arrangement of the manufactured customized impression tray relative to the patient's teeth.

The method may comprise visualizing the combined virtual model using e.g. a graphical display unit, such as a computer screen.

In some embodiments, said shaping of the virtual model is configured to provide that the centerline or the arch of the virtual model of the customized impression tray is substantially aligned with the arch of the digital 3D representation. I.e. in a visual presentation of the virtual model and the digital 3D representation the arches of these are aligned. The visual presentation may be of the combined model or of the virtual model and the digital 3D representation arranged in relation to each other according to a preferred arrangement for obtaining an impression of the set of teeth.

The centerline or the arch of the customized impression tray may be substantially aligned with the arch of the set of teeth, such that in the combined virtual model, the arch of the set of teeth is substantially aligned with the arch of the customized impression tray.

The offset may provide that the tooth-facing surfaces of the side-walls are moved away from the set of teeth and the wall-to-wall distance is increased. In the combined virtual model this corresponds to moving the virtual tooth-facing surfaces of the virtual model of the customized impression tray away from the tooth surfaces of the 3D digital representation. The moving away will then result in a larger distance between the tooth-facing surfaces of the manufactured customized impression tray and the teeth when the tray is arranged at the set of teeth.

In some embodiments, the method comprises controlling a lingual gap between the portion of the virtual model corresponding to the tooth facing surface of the lingual side-wall and the digital 3D representation of the set of teeth. The lingual gap provides a gap between the teeth and the lingual side-wall of the manufactured customized impression tray when the tray is arranged in relation to the patient's teeth.

In some embodiments, the method comprises controlling a labial gap between the portion of the virtual model corresponding to the tooth facing surface of the labial side-wall and the digital 3D representation of the set of teeth. The labial gap provides a gap between the teeth and the labial side-wall of the manufactured customized impression tray when the tray is arranged in relation to the patient's teeth.

The labial gap and the lingual gap may both vary along the arch of the set of teeth due to e.g. the variations in the shape of the teeth. The variation may be over the individual teeth and/or from tooth to tooth.

In some embodiments, the virtual model is shaped such that when the manufactured customized impression tray is arranged in relation to the set of teeth, the lingual gap may be below about 5 mm, such below about 4 mm, such as below about 3 mm, such as below about 2 mm. such as below about 1 mm.

In some embodiments, the virtual model is shaped such that when the manufactured customized impression tray is arranged in relation to the set of teeth, the labial gap may be below about 5 mm, such below about 4 mm, such as below about 3 mm, such as below about 2 mm. such as below about 1 mm.

The sum of the lingual gap and the labial gap may be below a maximum gap sum at least at a number of positions along the arch of the digital 3D representation of the set of teeth or along the arch of the set of teeth in the patient's mouth. These positions may be where the teeth have the largest width, i.e. the largest cross sectional dimension perpendicular to the arch of the set of teeth. The maximum gap sum may be in the range of about 0.5 mm to about 10 mm, such as in the range of about 2 mm to about 8 mm, such as in the range of about 4 mm to about 6 mm.

In some embodiments, the method comprises defining apertures in the virtual model of the customized impression tray, such that the corresponding apertures on the manufactured customized impression tray may provide a passage for excess impression material when customized impression tray is used to obtain the impression of the set of teeth.

The virtual apertures may be defined in the virtual model by indicating regions to be removed using 3D splines or by overlaying an aperture pattern onto the virtual model where the aperture pattern comprises a number of regions indicating where material should be virtually removed from the virtual model by e.g. a Boolean subtraction algorithm.

In some embodiments, the method comprises defining contact points on the virtual model of the customized impression tray, such that these contact points define the positions where contact is provided between the set of teeth and the manufactured customized impression tray when the tray is arranged at the patient's teeth. The contact points may e.g. be defined by an operator who indicates where on a visual representation one or more virtual contact points must be placed. The virtual contact points may take the form of protrusions formed by e.g. locally raising the surface of the virtual model or by virtually adding structures to the virtual model of the customized impression tray.

The virtual model may be configured to provide that only contact points defined on the gingiva-facing part of the manufactured customized impression tray are brought into contact with the patient's gums when the customized impression tray is arranged at the set of teeth.

In some embodiments, the virtual model is configured to provide that the gingiva-facing part of the manufactured customized impression tray, such as the gingiva-facing part of the side-walls, may be brought into contact with the patient's gums when the customized impression tray is arranged in relation to the set of teeth.

In some embodiments, the virtual model comprises a portion relating to an interconnecting base-wall arranged to connect the lingual side-wall to the labial side-wall. The base-wall may be arranged such that the base-wall together with the lingual and labial side-walls forms a U-shaped structure at least partly enclosing a space corresponding to a groove in the customized impression tray. Preferably, the base-wall is arranged to face the cusp or the incisal edge of the teeth when the customized impression tray is arranged in relation to the set of teeth.

In some embodiments, the portion relating to the base-wall is formed from a virtual plane that is generated based on the occlusal or incisal surfaces of the digital 3D representation of the set of teeth and offset away from the digital 3D representation.

The portions of the virtual model corresponding to the labial, occlusal and lingual tooth facing surfaces of the customized impression tray can then be combined virtually to form the virtual tooth facing surface of the virtual model.

In some embodiments, the portions of the virtual model corresponding to the tooth-facing surfaces are configured to provide a curved section at the transition between the portions relating to the side-walls and the portion relating to the base-wall. This provide that the virtual tooth facing surface is smooth without sharp corners such that the impression material more easily can separate from the tooth-facing surfaces of the manufactured customized impression tray when the impression is removed from the tray.

The set of teeth may comprise two or more of the mandibular teeth of the patient and the customized impression tray may be configured to be placed in relation to a part of or the entire mandibular arch of the patient's teeth.

The set of teeth may comprise two or more of the maxillary teeth of the patient and the customized impression tray may be configured to be placed in relation to a part of or the entire maxillary arch of the patient's teeth.

The customized impression tray may be configured for obtaining an impression of mandibular teeth or of maxillary teeth, and/or for obtaining an impression of mandibular teeth and of maxillary teeth.

The customized impression tray may comprise a handle. The handle may be a prefabricated structure onto which the walls of the tray are formed, or the handle may be formed together with the walls during the manufacturing of the customized impression tray.

In some embodiments, the virtual model is shaped such that direct contact between the patient's frenum and the manufactured customized impression tray is avoided when the tray is arranged in relation to the patient's teeth. This can be achieved by defining a 3D spline for the part of the virtual model facing the sulcus between the gingiva and e.g. the buccal tissue in the digital 3D representation, where this 3D spline is shaped such that virtual contact with the frenum part of the digital 3D representation is avoided. The contact may also be avoided by virtually removing material from the virtual model, such as with a virtual sculpting tool. The virtually removing may be adapted to provide that the shapes of the tooth-facing surfaces of the customized impression tray are configured to avoid contact with the frenum.

The frenum is the small pieces of skin that attach the lips, cheeks and tongue to the mouth. Examples include the piece of skin under the tongue which sticks out when a person picks his tongue and the piece of skin which sticks out when a person pull his lips. An advantage of this embodiment is that the discomfort arising from the contact between the prior art impression trays and the patient's frenum is avoided when using the customized impression tray.

In some embodiments, a slope between the opposing virtual tooth-facing surfaces of the side-walls is provided in the virtual model. The slope may provide that the wall-to-wall distance changes along the height of the teeth, such as increases towards the root end of the teeth compared to the distance at the cusp of the tooth.

In some embodiments, virtual impression transfer pins are comprised in the virtual model of the customized impression tray, such that the customized impression tray manufactured from the virtual model comprises corresponding transfer pins.

The different steps of a method according to the invention may appear in different orders. For example may a blocking out of undercuts be made before or after determining the arch of the set of teeth.

Disclosed is a non-transitory computer readable medium storing thereon a computer program, where said computer program is configured for causing computer-assisted processing to perform the method according to the invention, when the program code means are executed on the data processing system Disclosed is a method of manufacturing a customized impression tray adapted for being used in relation to obtaining an impression of a set of teeth, where the customized impression tray comprises a lingual side-wall and a labial side-wall, said method comprising:
a. obtaining a 3D digital representation of the set of teeth;
b. determining the arch of the set of teeth from said 3D digital representation;
c. virtually blocking out undercut regions in the 3D digital representation of said set of teeth;
d. obtaining a virtual model of the customized impression tray, wherein the virtual model is shaped according to the arch of the set of teeth; and
e. manufacturing the customized impression tray from said virtual model.

The surface defined by the virtually blocking out undercut regions may be offset to provide a virtual plane from which the tooth facing surfaces of the lingual side-wall and a labial side-wall are defined.

The wall-to-wall distance at different positions along the arch of the set of teeth may also be determined in addition to determining the arch.

The customization of the impression tray may provide that it fits a set of teeth of the patient more precisely than a mass manufactured impression tray thus reducing discomfort for the patient.

Disclosed is system for manufacturing a customized impression tray adapted for being used in relation to obtaining an impression of a set of teeth, where the customized impression tray comprises a lingual side-wall and a labial side-wall, said system comprising:
a): means for obtaining a 3D digital representation of the set of teeth, where said 3D digital representation comprises a labial surface and a lingual surface of the set of teeth;
b): means for generating a virtual model of the customized impression tray, where the virtual model comprises portions corresponding to tooth-facing surfaces of the labial and lingual side-walls, and where said generating comprises shaping the virtual model of the customized impression tray according to the 3D digital representation; and
c): means for manufacturing the customized impression tray from said virtual model.

Furthermore, the invention relates to a computer program product comprising program code means for causing a data processing system to perform the method according to the invention, when said program code means are executed on the data processing system, and a computer program product, comprising a computer-readable medium having stored there on the program code means.

Scanning an object in a 3D scanner for obtaining a 3D digital representation of the surface of the object may relate to the process of developing a mathematical representation of the surface of the object via specialized software. The 3D digital representation may represent the object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner describes the distance to a surface at each point in the picture.

For most situations, a single scan will not produce a complete model of the object. Multiple scans, such as 5, 10, 12, 15, 20, 30, 40, 50, 60, 70, 80, 90 or in some cases even hundreds, from many different directions may be required to obtain information about all sides of the object. These scans are brought in a common reference system, a process that may be called alignment or registration, and then merged to create a complete model.

A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time.

An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

The present invention relates to different aspects including the method and system described above and in the following, and corresponding methods, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

In the following description, reference is made to the accompanying figures, which show by way of illustration how the invention may be practiced.

Figure 1:
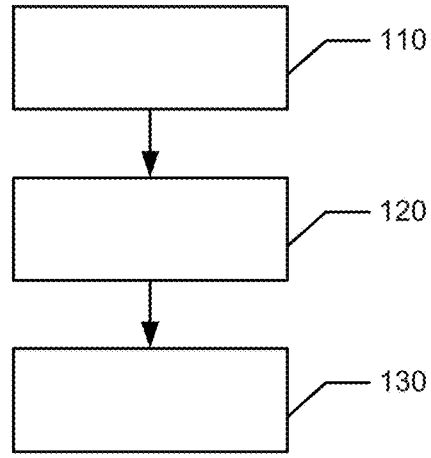
FIG. 1 shows a flow chart of an embodiment of the method.

FIG. 1 shows a flow chart of an embodiment of the method of manufacturing a customized impression tray adapted for being used in relation to obtaining an impression of a set of teeth. The customized impression tray comprises a lingual side-wall and a labial side-wall.

In step 110 a 3D digital representation of the set of teeth is obtained, where said 3D digital representation comprises a labial surface and a lingual surface of the set of teeth.

In step 120 a virtual model of the customized impression tray is generated, where the virtual model comprises portions corresponding to the tooth-facing surfaces of the tray's labial and lingual side-walls, and where said generating comprises shaping the virtual model of the customized impression tray according to the 3D digital representation.

In step 130 the customized impression tray is manufactured from said virtual model.

Figure 2:
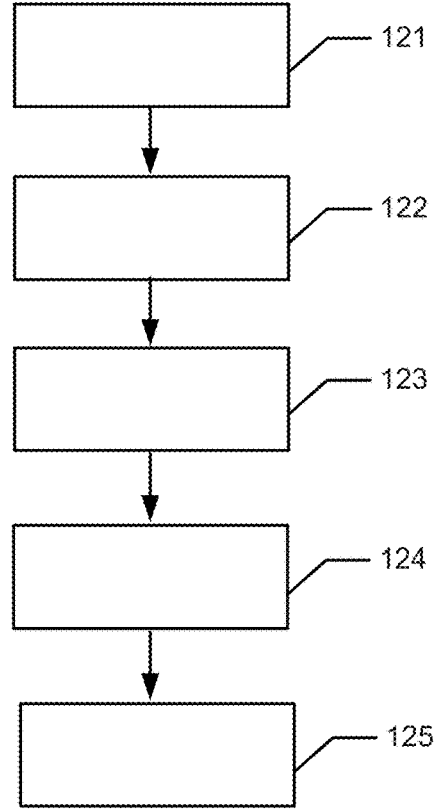
FIG. 2 shows a flow chart for generating a virtual model of the customized impression tray.

FIG. 2 shows a flow chart for generating a virtual model of the customized impression tray.

In step 121, the insertion direction of the customized impression tray is determined. The insertion direction describes the movement of the customized impression tray towards the set of teeth. The insertion direction may be indicated with an elongated structure visualized together with the 3D digital representation of the set of teeth on a graphical display unit. Using a pointing tool, such as a computer mouse, the insertion direction may be adjusted by the operator. The insertion direction may be equal to a normal of the occlusal plane of the teeth for which an impression is to be obtained, such as the normal to the occlusal plane of the mandibular arch or of the maxillary arch.

In step 122, the undercut regions are identified from the shape of the teeth as described by the 3D digital representation and from the chosen insertion direction, and the undercut regions are virtually blocked out. An initial position and shape of a virtual plane is then defined from the blocked-out surface of the 3D digital representation, such that the virtual plane initially coincides with the blocked out 3D digital representation in the blocked out region. Virtual planes are defined both on the labial side and on the lingual side of the teeth.

The virtual blocking out undercut regions may be realized using computer implemented algorithms known to the skilled person.

In step 123, an offset away from the corresponding teeth in the digital 3D representation is provided to the virtual planes. The virtual model is then shaped based on the one or more offset virtual planes, i.e. the portions of the virtual model relating to the tooth-facing surfaces of the labial and lingual side-walls are shaped based on the offset virtual planes. The portions relating to the tooth-facing surfaces may be configured to be substantially parallel with the virtual planes and to coincide with the offset virtual plane over at least a part of the tooth-facing surface. The offsets of the virtual planes away from the corresponding teeth in the digital 3D representation provide that the wall-to-wall distance of the side-walls of the manufactured customized impression tray increases. The offsets also provide that the distance between the tooth facing surfaces of the side-walls and the labial and lingual surfaces of the patient's teeth increases. The size of the offsets may be entered by the operator using a keyboard or a pointer tool.

In step 124, the portion of the virtual model relating to a gingiva-facing part of the side-walls is defined. This may be done by defining and potentially adjusting the form of a 3D spline representing the gingiva-facing part.

In step 125, contact points configured for establishing the physical contact between the customized impression tray and the patient's oral cavity along with specific contact-free areas (such as the frenum) are defined for the virtual model. The contact areas and contact-free areas may also be defined using 3D splines FIG. 3 shows a schematic drawing where the customized impression tray is arranged in relation the set of teeth for obtaining an impression of the set of teeth.

In this drawing the set of teeth 340 is illustrated by a longitudinal section of one of the left maxillary teeth with a labial surface 341, a lingual surface 342 and an occlusal surface 343 of the tooth. The gingiva 344 is also indicated. The customized impression tray 350 comprises a labial side-wall 351, a lingual side-wall 352 and an occlusal side-wall 353. The occlusal side-wall may also be referred to as a base-wall. The side-walls have respective tooth-facing surfaces 3511, 3521, 3531 facing the teeth when the customized impression tray 350 is arranged at the set of teeth 340. The labial side-wall 351 and the lingual side-wall 352 each comprise a gingiva-facing part 3512, 3522. The wall-to-wall distance between opposing tooth-facing surfaces of the lingual side-wall and the labial side-wall is marked with the bar 355. When the manufactured customized impression tray is used for obtaining an impression of the set of teeth, the impression material is distributed in the space 354 located between the surfaces of the teeth 341, 342, 343 and the tooth-facing surfaces 3511, 3521, 3531.

Figure 3:
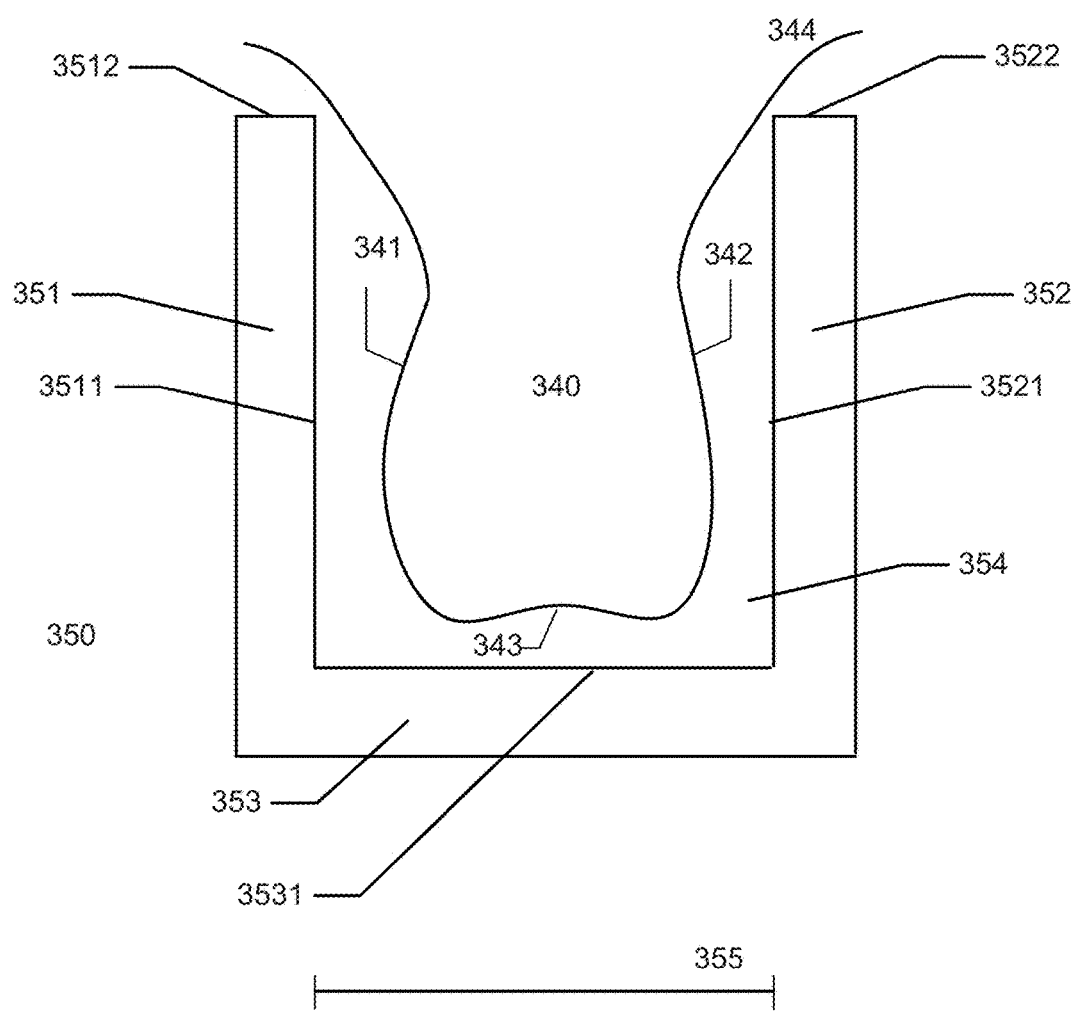
FIG. 3 shows a schematic of the customized impression tray and the set of teeth.

FIG. 3 can also be used to illustrate the virtual model of the customized impression tray and to illustrate the combined virtual model comprising the virtual model of the customized impression tray and the 3D digital representation of the set of teeth.

The virtual model comprises portions relating to the tooth facing surfaces and portions relating to the gingival facing surfaces of the customized impression tray. The reference numbers used above in relation to the customized impression tray then refer to their equivalents of the virtual model of the customized impression tray, and the reference numbers used in relation to the set of teeth then refer to their equivalents of the 3D digital representation of the set of teeth.

Figure 4:
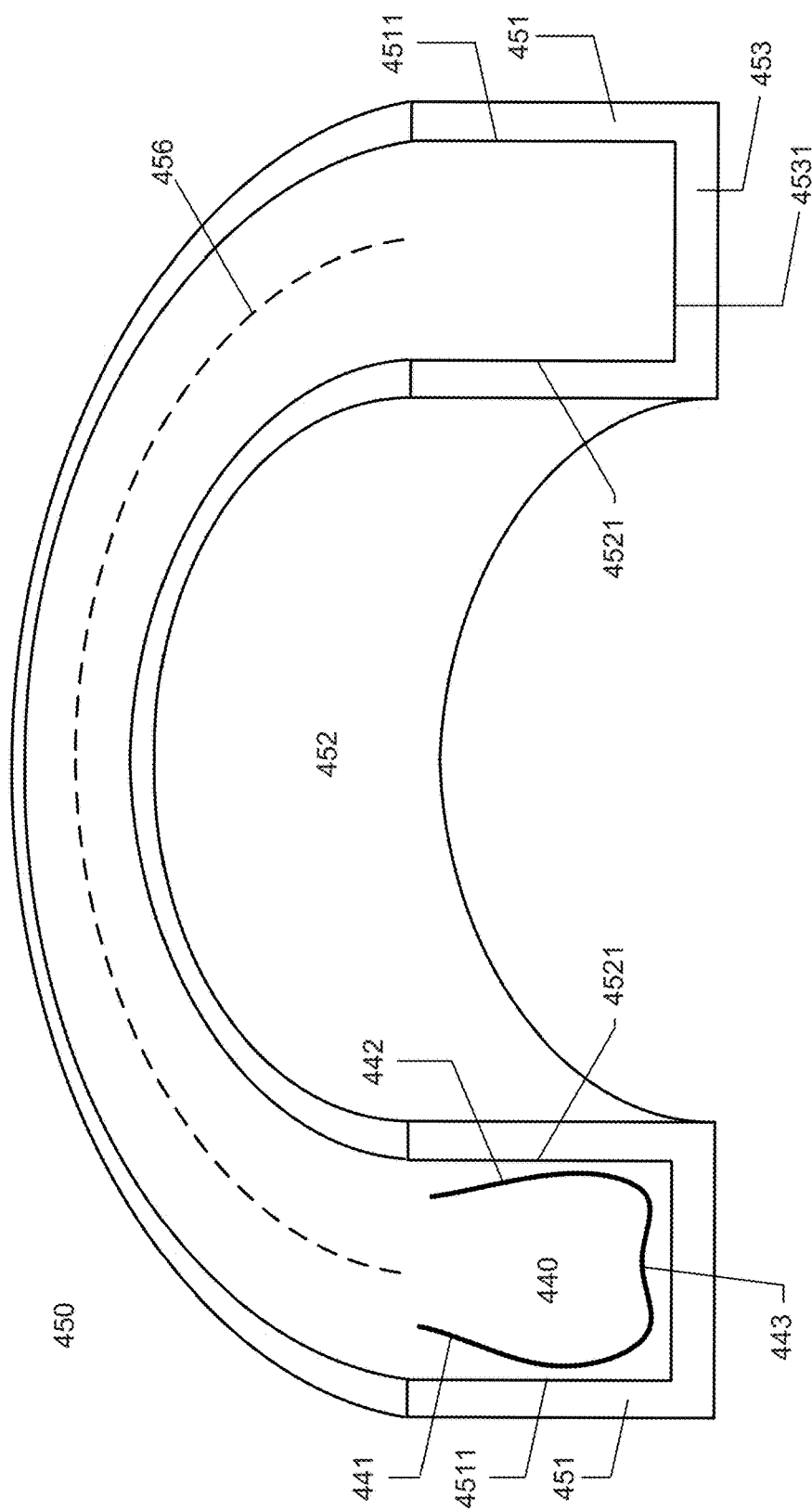
FIG. 4 shows an illustration of a customized impression tray.

FIG. 4 shows an illustration of a customized impression tray configured to be used in the process of obtaining an impression of the entire arch of the maxillary teeth.

The set of teeth 440 is illustrated by a longitudinal section of one of the left maxillary teeth with a labial surface 441, a lingual surface 442 and an occlusal surface 443 of the tooth.

The customized impression tray 450 comprises a labial side-wall 451, a lingual side-wall 452 and an occlusal side-wall 453. The side-walls 451, 452, 453 have respective tooth-facing surfaces 4511, 4521, 4531 facing the teeth when the customized impression tray 450 is arranged at the set of teeth 440.

A centerline 456 of the customized impression tray is also indicated. The centerline is here substantially identical to the arch of the customized impression tray.

Figure 5A:
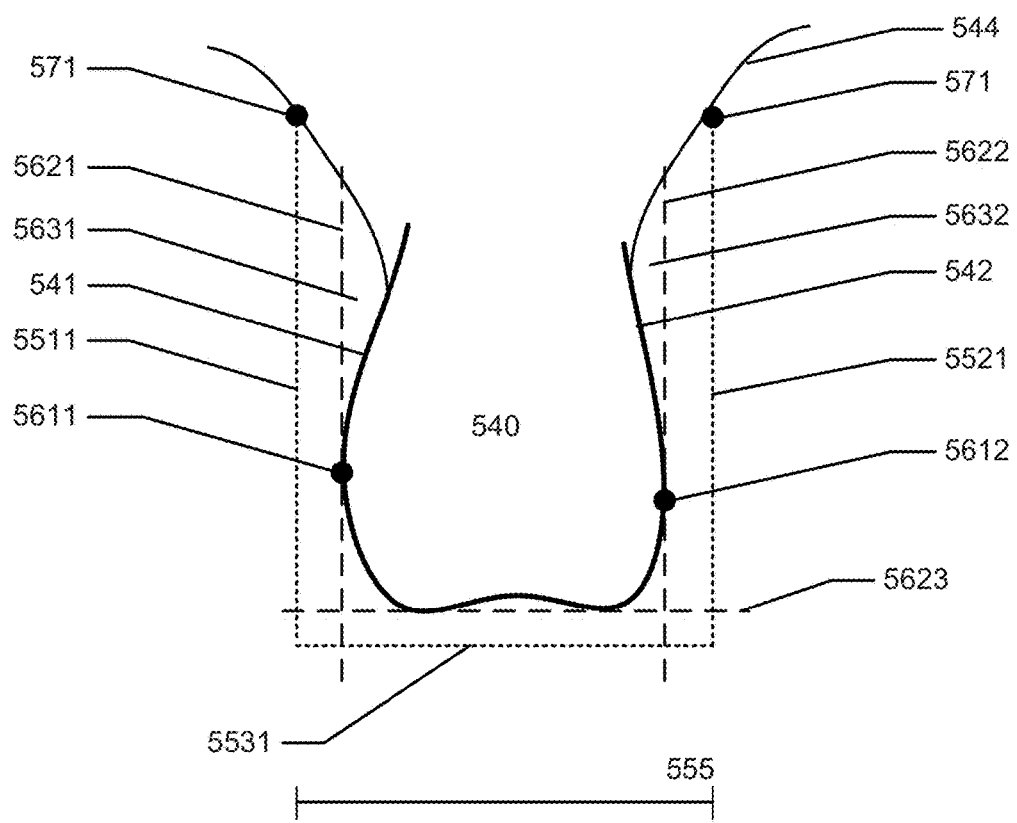
FIG. 5 shows an example of how portions of the virtual model can be shaped according to the 3D digital representation.

FIG. 5a shows an illustration of how the portions of the virtual model relating to opposing tooth facing surfaces can be shaped according to the 3D digital representation.

The digital 3D representation of the tooth 540 has a concave surface and the apexes 5611, 5612 of the labial surface 541 and the lingual surface 542, respectively, are determined. The undercut regions 5631, 5632 are virtually blocked out to avoid the undercuts thereby forming blocked out surfaces 5621, 5622 from which virtual planes are created. The virtual planes are then offset such that offset virtual planes 5511, 5521 are defined. These virtual planes may extend along the arch of the set of teeth. The shape of the offset virtual planes along the arch may be defined only by the widest parts of the teeth in the set of teeth, such that the offset virtual planes are smooth without noticeable variation over the individual teeth.

In the virtual model of the customized impression tray, the shape of the portions relating to the tooth-facing surfaces of the side-walls are then be determined from the offset virtual planes 5511, 5521.

The relative position of the portions relating to the tooth-facing surfaces after the offset has been applied defines the wall-to-wall distance between the corresponding tooth facing surfaces of the side-walls of the customized impression tray.

An occlusal virtual plane 5623 is defined in relation to the occlusal surface of the tooth in the digital 3D representation. In the figure, the occlusal virtual plane is flat and is aligned with the extreme of the occlusal surface. Alternatively, the occlusal virtual plane 5623 can be shaped according to the occlusal surface of the tooth. An offset is provided to the occlusal virtual plane 5623 such that an offset virtual plane 5531 is defined.

The virtual tooth facing surface of the virtual model of the customized impression tray is then formed from the offset virtual planes 5511, 5521, 5531, such that a groove is defined in which impression material can be arranged in the manufactured customized impression tray.

The magnitude of the offsets may be determined by an operator entering data into a computer program using e.g. a keyboard or another type of interface. The magnitude of the labial, lingual and occlusal offsets may be changed independently.

The offsetting of surfaces and the forming of the virtual tooth facing surface from the offset surfaces can be realized using computer implemented algorithms known to the skilled person.

The shape of the gingiva-facing portion of the virtual model can be determined using a 3D spline 571 defined in relation to the digital 3D representation of the set of teeth.

Figure 5B:
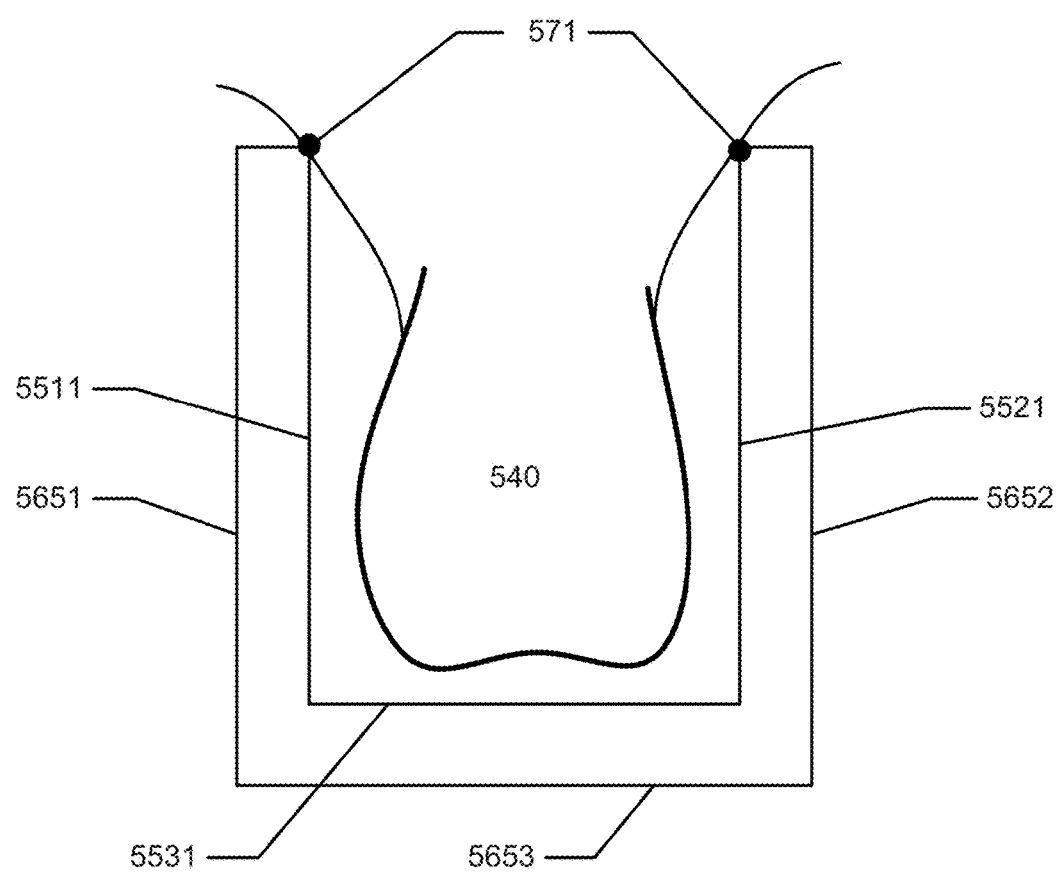

FIG. 5b shows how the portions of the virtual model relating to the outer surfaces of the tray are formed by shelling. The shelling creates virtual outer surfaces 5651, 5652, 5653 which together forms the virtual outer surface facing away from the tooth. The virtual tooth facing surface and the virtual outer surface facing may need to be connected by a loofting process forming a surface connecting the two and forming a virtual gingival facing surface of the virtual model. With all surfaces created such that a water-tight virtual model is defined, the customized impression tray can be manufactured.

In the illustrated example, the 3D spline 571 is defined at the gingiva such that virtual planes reach the gingiva of the digital 3D representation. In this case, the manufactured customized impression tray is configured to rest on the gingiva when the impression is taken. This has the advantage that the dentist is certain that there is space for impression material between the occlusal tooth facing surface of the tray and the occlusal surface of the teeth such that a proper impression is obtained at the occlusal surface of the teeth.

Figure 6:
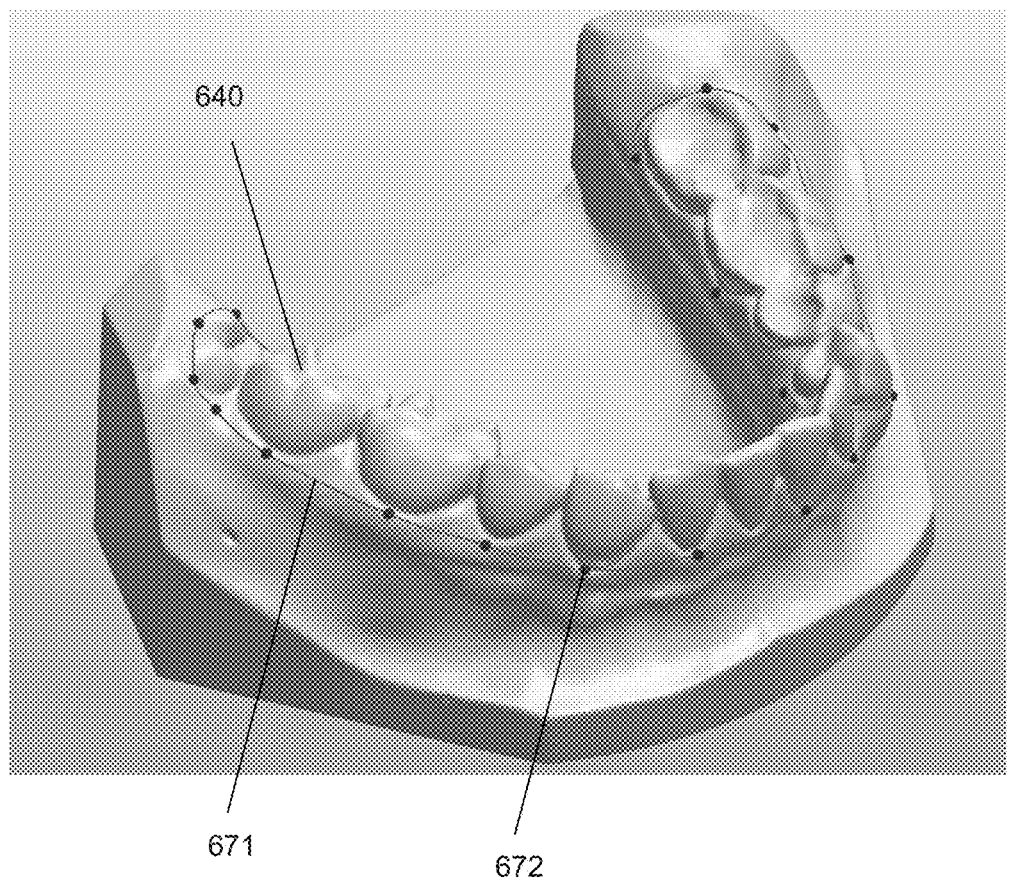
FIG. 6 shows a visual presentation of a 3D digital representation of a set of teeth with a 3D spline defining the shape of a gingiva-facing part of a customized impression tray.

FIG. 6 shows a visual presentation of a 3D digital representation of a set of teeth with a 3D spline defining the shape of a gingiva-facing part of a customized impression tray.

The 3D spline 671 may be defined by an operator who marks a number of control points 672 on the visual presentation of the 3D digital representation 640. Standard computer-implemented algorithms may then define the 3D spline from these control points. The 3D spline 671 may also be derived automatically from the 3D digital representation 640 and then optionally adjusted by an operator by moving the control points 672 relative to the 3D digital representation 640.

Figure 7A:
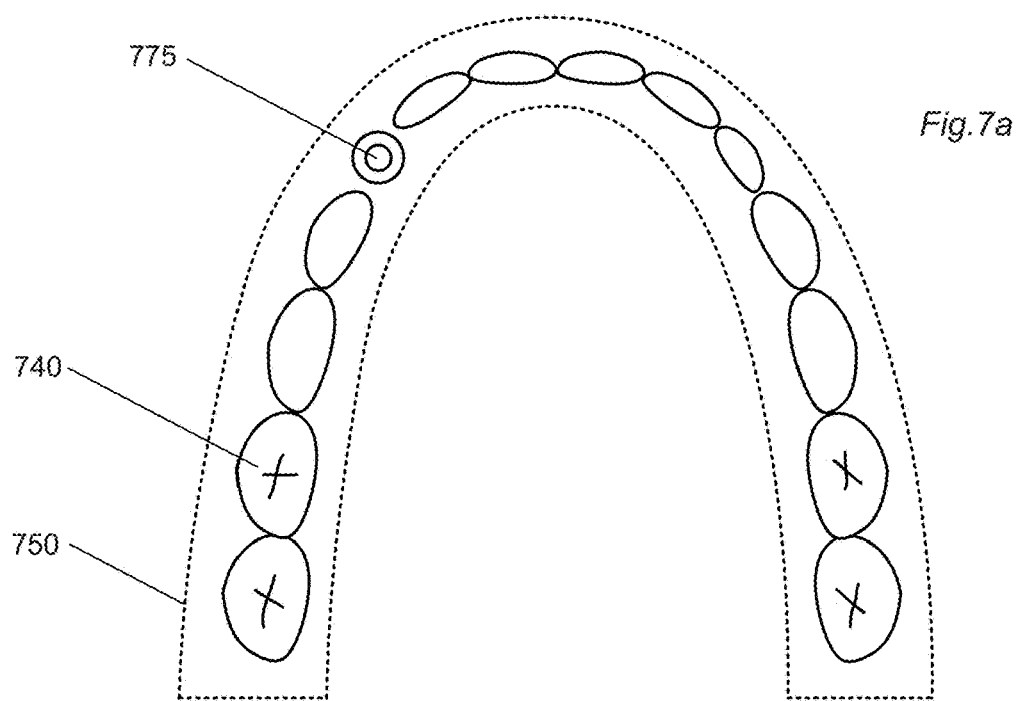
FIG. 7 shows a schematic for the case where the set of teeth comprises an implant.

The 3D spline 671 may then be used for shaping the gingiva-facing portion of the virtual model of the customized impression tray FIG. 7a shows a digital 3D representation of a set of teeth 740 comprising a dental implant 775 arranged in the patient's bone structure. The location and orientation of the dental implant can be determined from e.g. scan flags or a healing abutment arranged in the implant while scanning the patient's set of teeth. The location of the virtual model of the customized impression tray 750 when arranged at the set of teeth is also indicated.

Figure 7B:
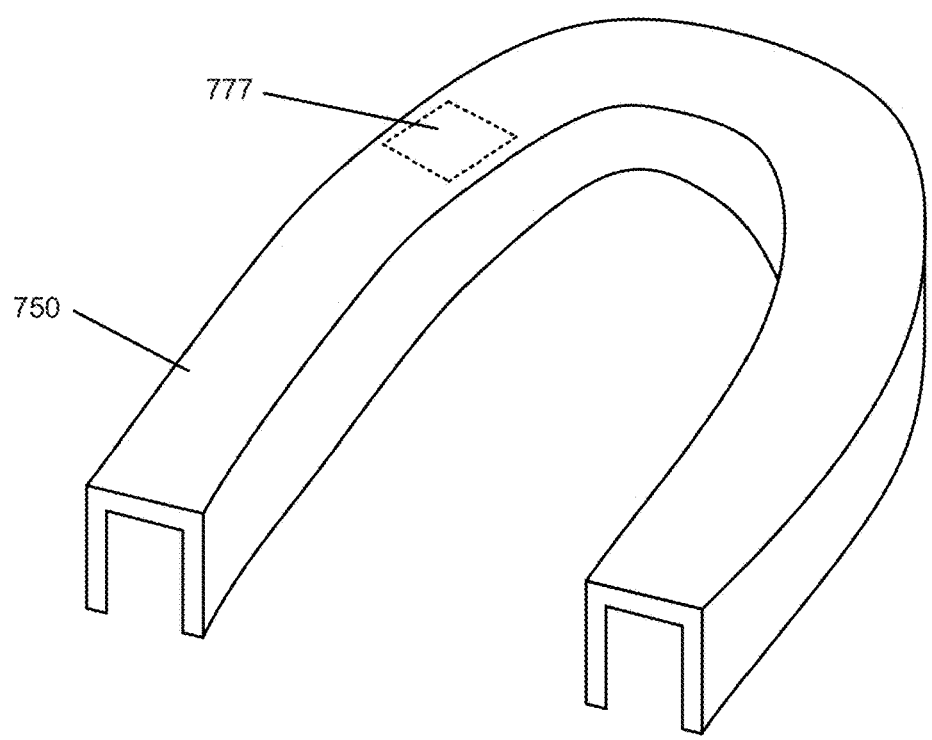

FIG. 7b shows the part 777 of the virtual model of the customized impression tray 750 corresponding to the implant position. In some embodiments of the invention, this part is virtually removed from the virtual model of the customized impression tray such that there is an opening in the manufactured customized impression tray which allows access to the implant even when the tray is arranged at the set of teeth.

FIG. 8 shows how an opening can be defined in the virtual model of the customized impression tray.

Figure 8A:
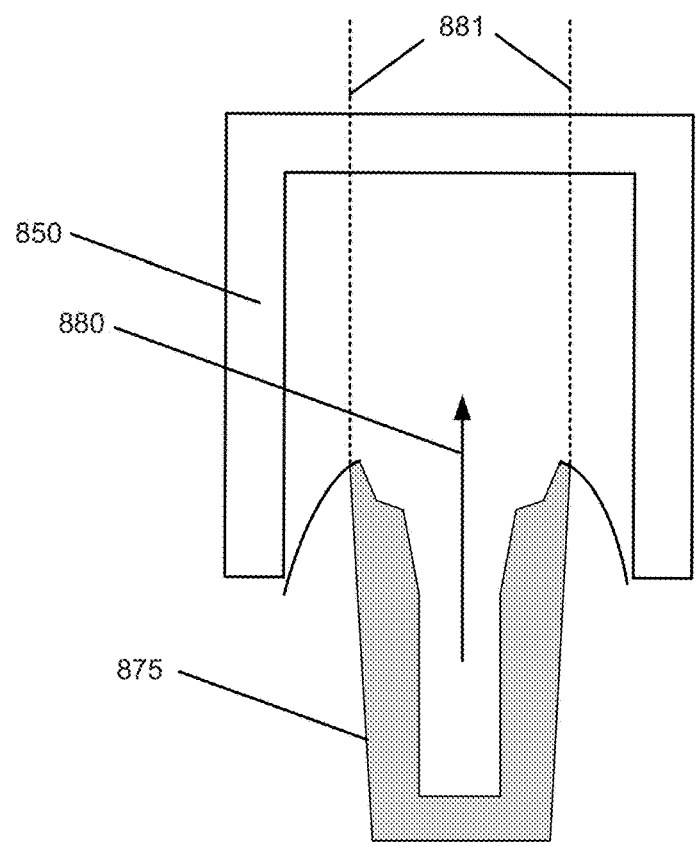
FIG. 8 shows how an opening can be defined in the virtual model of the customized impression tray.

FIG. 8a shows a cross sectional view of the digital 3D representation at the site of the implant with the customized impression tray arranged at the set of teeth. In this example, the dental implant 875 is located in the mandibular bone and defines an implant orientation 880. The orientation 880 and location of the implant can be determined by having a healing abutment arranged in the implant while scanning the set of teeth. A cylinder (here indicated by its boundary 881) is defined from the implant orientation 880 such that the cylinder is aligned with the dental implant 875 and extends along the implant orientation 880 to intersect the virtual model of the customized impression tray 850. The cross section of the cylinder can be have the shape of a circle, an ellipse, a parabola, a hyperbola, a rectangle, a square, or a triangle. An opening in the virtual model of the customized impression tray is defined by subtracting the cylinder 881 from the virtual model of the customized impression tray 850.

Figure 8B:
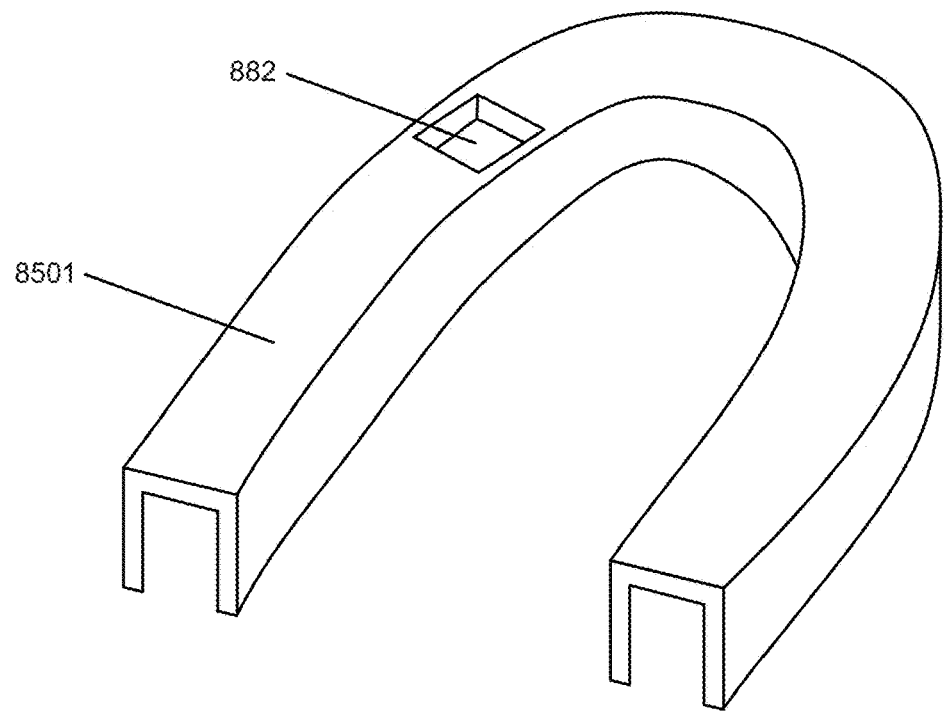

FIG. 8b shows the customized impression tray 8501 manufactured from virtual model with the opening 882 providing access to the implant event when the tray is arranged at the set of teeth.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for manufacturing a customized impression tray comprising labial and lingual side-walls, where said customized impression tray is for obtaining an impression of a set of teeth and/or gingiva of a patient, said method comprising:
   a) obtaining a 3D digital representation of the set of teeth and/or gingiva using a hardware processor, wherein the 3D digital representation of the set of teeth and/or gingiva was acquired by a scanner that scanned at least one of the teeth and/or gingiva of the patient, a physical model of the set of teeth and/or gingiva, or an impression of the set of teeth and/or gingiva, where said 3D digital representation comprises a labial surface and a lingual surface of the set of teeth and/or gingiva;
   b) generating, by the hardware processor, the virtual model of the customized impression tray based on the 3D digital representation of the set of teeth and/or gingiva, where the virtual model comprises portions corresponding to surfaces of the labial and lingual side-walls facing surfaces of the set of teeth and/or gingiva; and
   c) manufacturing the customized impression tray from the virtual model,
   wherein generating the virtual model comprises defining virtual apertures in the virtual model of the customized impression tray, such that the corresponding apertures on the manufactured customized impression tray provide a passage for excess impression material when the customized impression tray is used to obtain the impression of the set of teeth and/or gingiva;
   wherein the virtual apertures are defined in the virtual model by indicating regions to be removed using 3D splines or by overlaying an aperture pattern onto the virtual model where the aperture pattern comprises a number of regions indicating where material should be virtually removed from the virtual model.

2. The method according to claim 1, wherein generating the virtual model comprises defining one or more virtual planes in relation to the 3D digital representation, and wherein the virtual model is shaped based on the one or more virtual planes.

3. The method according to claim 2, wherein said one or more virtual planes at least in part is defined by virtually blocking out undercut regions at the 3D digital representation.

4. The method according to claim 2, wherein an offset away from the corresponding teeth and/or gingiva in the 3D digital representation is provided to the one or more virtual planes, such that the virtual model is shaped based on the one or more offset virtual planes.

5. The method according to claim 4, wherein the offset corresponds to a shelling of a region of the 3D digital representation.

6. The method according to claim 1, wherein generating the virtual model comprises determining a boundary of the virtual model.

7. The method according to claim 6, wherein the boundary of the virtual model is described by a 3D spline.

8. The method according to claim 1, wherein the customized impression tray is configured for use in relation to a dental implant procedure, and wherein said generating the virtual model of the customized impression tray comprises considering a location and orientation of an implant.

9. The method according to claim 8, wherein generating the virtual model comprises defining an opening in the virtual model of the customized impression tray at a part corresponding to the location of the implant.

10. The method according to claim 9, wherein a size and location of the opening is determined from an implant treatment plan.

11. The method according to claim 10, wherein the implant treatment plan comprises designing a drill guide configured for guiding a drilling of an implant hole.

12. The method according to claim 9, wherein the opening is defined by subtracting a cylinder from the virtual model of the customized impression tray, where said cylinder is aligned with the orientation of the implant.

13. The method according to claim 9, wherein the opening is designed to be larger than an area of a top of the implant to account for inaccuracies in implant orientation and/or position.

14. The method according to claim 1, where the method comprises determining an arch of the set of teeth from said 3D digital representation and based on that arch define a centerline or an arch of the virtual model of the customized impression tray.

15. The method according to claim 1, wherein generating the virtual model comprises controlling a lingual gap between a portion of the virtual model corresponding to a tooth facing surface of the lingual side-wall and the 3D digital representation and/or controlling a labial gap between a portion of the virtual model corresponding to a tooth facing surface of the labial side-wall and the 3D digital representation.

16. The method according to claim 1, wherein generating the virtual model comprises defining contact points on the virtual model of the customized impression tray, such that these contact points define positions where contact is provided between the set of teeth and/or gingiva and the manufactured customized impression tray when the tray is arranged on the set of teeth and/or gingiva of a patient.

17. The method according to claim 1, wherein the virtual model comprises a portion relating to an interconnecting base-wall arranged to connect the lingual side-wall to the labial side-wall, and portions of the virtual model corresponding to the surfaces facing the set of teeth and/or gingiva are configured to provide a curved section at the transition between portions relating to the side-walls and portions relating to the base-wall.

18. The method according to claim 1, wherein generating the virtual model comprises adapting the virtual model of the customized impression tray such that direct contact with a frenum of a patient is avoided when the manufactured customized impression tray is arranged on the set of teeth and/or gingiva of the patient.

19. The method according to claim 1, wherein the 3D digital representation of the set of teeth and/or gingiva consists of data relating to gingiva of a patient.

20. The method according to claim 1, wherein impression transfer pins are comprised in the virtual model of the customized impression tray.

21. A method of manufacturing a customized impression tray adapted for being used in relation to obtaining an impression of a set of teeth and/or gingiva of a patient where the customized impression tray comprises a lingual side-wall and a labial side-wall, said method comprising:
a) obtaining a 3D digital representation of the set of teeth and/or gingiva, where said 3D digital representation comprises a labial surface and a lingual surface of the set of teeth and/or gingiva;
b) generating a virtual model of the customized impression tray based on the digital 3D representation of the set of teeth and/or gingiva, where the virtual model comprises portions corresponding to surfaces of the labial and lingual side-walls facing surfaces of the set of teeth and/or gingiva; and
c) manufacturing the customized impression tray from said virtual model, the customized impression tray comprising apertures which provide a passage for excess impression material when the customized impression tray is used to obtain the impression of the set of teeth and/or gingiva;
wherein virtual apertures are defined in the virtual model by indicating regions to be removed using 3D splines or by overlaying an aperture pattern onto the virtual model where the aperture pattern comprises a number of regions indicating where material should be virtually removed from the virtual model.

* * * * *